US005512666A

United States Patent [19]

McCurry, Jr. et al.

[11] Patent Number: 5,512,666

[45] Date of Patent: Apr. 30, 1996

[54] PROCESS FOR MAKING ALKYL POLYGLYCOSIDES

[75] Inventors: Patrick M. McCurry, Jr., Lansdale, Pa.; Janet R. Varvil, West Chester; Carl E. Pickens, Fairfield, both of Ohio

[73] Assignee: Henkel Corporation, Plymouth Meeting, Pa.

[21] Appl. No.: 278,777

[22] Filed: Jul. 22, 1994

[51] Int. Cl.$^{6}$ .......... C07H 15/04

[52] U.S. Cl. .......... 536/18.6; 536/124

[58] Field of Search .......... 536/18.6, 124

[56] References Cited

U.S. PATENT DOCUMENTS

| | | | |
|---|---|---|---|
| 3,102,149 | 8/1963 | Barry | 260/621 |
| 3,203,872 | 8/1965 | Baumann | 292/40 |
| 3,450,690 | 6/1969 | Gibbons et al. | 260/210 |
| 3,772,269 | 11/1973 | Lew | 260/210 R |
| 3,928,318 | 12/1975 | Panusch et al. | 260/210 R |
| 4,329,449 | 5/1982 | Roth et al. | 536/18.6 |
| 4,393,203 | 7/1983 | Mao et al. | 536/124 |
| 4,465,828 | 8/1984 | Rau et al. | 536/18.6 |
| 4,483,979 | 11/1984 | Mao | 536/18.6 |
| 4,762,918 | 8/1988 | McDaniel, Jr. et al. | 336/127 |
| 4,797,478 | 1/1989 | Lebuhn et al. | 536/18.5 |
| 4,820,814 | 4/1989 | Lueders | 536/127 |
| 4,866,165 | 9/1989 | Lueders | 536/18.6 |
| 4,889,925 | 12/1989 | Schmid et al. | 536/18.6 |
| 4,923,976 | 5/1990 | Arnaudis | 536/18.6 |
| 4,939,246 | 7/1990 | Baur | 536/18.6 |
| 4,950,743 | 8/1990 | McCurry, Jr. et al. | 536/18.6 |
| 4,959,468 | 9/1990 | Ravi et al. | 536/127 |
| 4,988,807 | 1/1991 | Christensen et al. | 536/127 |
| 4,990,605 | 2/1991 | Lueders | 536/18.5 |
| 5,130,420 | 7/1992 | Yamamuro et al. | 536/18.6 |

FOREIGN PATENT DOCUMENTS

| | | |
|---|---|---|
| 0077167 | 4/1983 | European Pat. Off. . |
| 0102558 | 3/1984 | European Pat. Off. . |
| 0249031 | 12/1987 | European Pat. Off. . |
| 0099183 | 1/9184 | European Pat. Off. . |
| 0688747 | 3/1953 | United Kingdom . |
| 0933698 | 8/1963 | United Kingdom . |
| 2131802 | 6/1984 | United Kingdom . |

OTHER PUBLICATIONS

H. Steinberg, "Organoboron Chemistry", John Wiley & Sons, Inc. (1964), vol. 1, pp. 161–181).

L. F. Fieser & M. Fieser, "Organic Chemistry", D. C. Heath & Co., Boston (1944) pp. 137–146.

"The Basics Of Industrial Oleochemistry", G. Dieckermann & H. J. Heinz (1988) pp. 33–42 & 177–180.

CA 48:2756f.

"Preparation and Rate of Hydrolysis of Boric Acid Esters", Howard Steinberg & D. L. Hunter (U.S. Borax & Chemical Co.), Ind. Eng. Chem. (1957) 49, pp. 174–181.

*Primary Examiner*—John W. Rollins

*Attorney, Agent, or Firm*—Wayne C. Jaeschke; John E. Drach; Henry E. Millson, Jr.

[57] ABSTRACT

A process has been discovered for making alkyl polyglycoside which comprises reacting a fatty alcohol having from about 8 to about 22 carbon atoms with a sugar, in the presence of an acid catalyst, to form a product of alkyl polyglycoside and excess fatty alcohol. The molar ratio of fatty alcohol to sugar, respectively, is at least 2:1. The excess fatty alcohol is then separated from the alkyl polyglycoside product. Once separated, the excess fatty alcohol is then reacted with a source of boric acid to form a mixture comprised of one or more borate esters of the fatty alcohol and inert compounds. The non-hydroxylic compounds are then separated from the borate esters. The substantially pure fatty alcohol is then returned to the beginning of the process for use in the formation of alkyl polyglycoside.

27 Claims, No Drawings

PROCESS FOR MAKING ALKYL POLYGLYCOSIDES

BACKGROUND OF THE INVENTION

1. Field of the Invention

This invention relates to an improved method for preparing alkyl polyglycosides which includes the reaction of glucose and a fatty alcohol. More specifically, the present invention relates to a method for preparing alkyl polyglycosides which utilizes recycled fatty alcohol wherein elevated levels of interfering contaminants are periodically removed from the recycled fatty alcohol, and recycles the purified fatty alcohol.

2. Description of the Related Art

Alkyl polyglycosides are conveniently prepared by reacting an alcohol of the type and chain length which is desired, usually a fatty alcohol from which is derived the "alkyl" portion of the glycoside of interest, with a saccharide reactant (e.g., a monosaccharide such as glucose, xylose, arabinose, galactose, fructose, etc., or a polysaccharide such as starch, hemicellulose, lactose, maltose, melibiose, etc.) or with a glycoside starting material wherein the aglycone portion thereof is different from the alkyl substituent desired for the ultimate alkyl polyglycoside product of interest. Typically, these reactions are conducted at elevated temperatures and reduced pressures and in the presence of an acid catalyst and using a 2–10 molar ratio of fatty alcohol to monosaccharide. After the reaction has been terminated, usually by the addition of base, the excess fatty alcohol is reclaimed from the alkyl polyglycoside product by removing it by distillation under reduced pressure. The reclaimed, distilled fatty alcohol typically contains various types of co-distilling impurities, some of which were generated in the alkyl polyglycoside reaction and others which entered the process as impurities in "virgin" alcohol. Examples of the former include fatty esters of formic and levulinic acids (solvolysis products of the well-documented saccharide dehydration product HMF, or 5-hydroxymethyl furfural), as well as lactate and acetate esters and various ethers. In addition, other non-alcohol components are found in reclaimed alcohol which can be traced to impurities found in "virgin" fatty alcohols. The concentrations of some of these impurities are seen to diminish after the glycosidation reaction. Examples of these "reactive" impurities are fatty aldehydes, which disappear by acetalization reactions during the glycosidation step. The concentrations of other, so-called "inert" impurities present in "virgin" alcohols are found to increase each time the reclaimed alcohol is reused in the glycosidation reaction. The majority of these impurities result from the manufacturing process or storage of the alcohols themselves. The exact chemical nature of such impurities depends upon the raw materials and manufacturing processes used, and storage conditions. Examples of by-product impurities formed during the manufacturing of "naturally"-derived alcohols are hydrocarbons having 3 and/or 4 more carbon atoms than each of those in the fatty alcohols used, and various ethers having molecular weights comparable to the aforementioned hydrocarbons. The use of repeatedly recycled fatty alcohol which contains a build-up of inerts and other impurities in the process for making alkyl polyglycosides results in a product having less than desirable color and composition and a lower overall product yield.

Therefore, it is an object of the present invention to provide a process for making an alkyl polyglycoside by reacting a sugar and a fatty alcohol to obtain an alkyl polyglycoside and unreacted fatty alcohol reaction product wherein the unreacted fatty alcohol is then separated from the alkyl polyglycoside and recycled. Periodically, the recycled fatty alcohol is substantially purified by removal of all non-hydroxylic impurities, including esters, ethers and hydrocarbons.

SUMMARY OF THE INVENTION

A process has been discovered for making alkyl polyglycosides which comprises reacting a fatty alcohol having from about 8 to about 22 carbon atoms with a sugar, in the presence of an acid catalyst, to form a product of alkyl polyglycoside and excess fatty alcohol. The feed molar ratio of fatty alcohol to sugar, respectively, is at least 2:1. The excess, unreacted fatty alcohol is then separated from the alkyl polyglycoside product. The excess, unreacted fatty alcohol contains a number of both non-hydroxyl and hydroxyl-containing contaminants which accumulate upon repeated recycles and which must be removed after reaching an unacceptable amount. Once separated, the excess fatty alcohol is contacted with a source of polybasic acid such as boric acid, trimethyl borate, phosphoric acid, phosphoryl chloride, phosgene, phosphorus trichloride, and sulfuryl chloride so that the hydroxylic contaminants react with a polybasic acid source to form a mixture comprised of one or more polybasic acid-fatty alcohol esters and unreacted, non-hydroxylic (including "inert") compounds. The non-hydroxylic components are then separated from the polybasic acid esters. A substantially pure fatty alcohol is then formed by hydrolyzing the recovered polybasic acid ester mixture. The substantially pure, but water saturated, fatty alcohol is then returned to the beginning of the process for use in the formation of alkyl polyglycoside product. Drying can be automatically accomplished in situ prior to glycosidation. An alkyl polyglycoside made by the processes according to the invention exhibits improved yield, composition and color, as compared to alkyl polyglycosides made by using the corresponding recycled fatty alcohol which has not been treated by the method according to the present invention.

DESCRIPTION OF THE PREFERRED EMBODIMENTS

Other than in the operating examples, or where otherwise indicated, all numbers expressing quantities or ingredients or reaction conditions used herein are to be understood as modified in all instances by the term "about".

One method for making an alkyl polyglycoside comprises reacting a fatty alcohol and a sugar at an elevated temperature and reduced pressure in the presence of an acid catalyst, using at least 2 moles of fatty alcohol per mole of sugar. After the reaction has been terminated, the excess unreacted fatty alcohol is usually reclaimed from the alkyl polyglycoside product by fractional distillation under reduced pressure. The distilled fatty alcohol is then combined with about 10–20%, by weight, of make-up (virgin) fatty alcohol and recycled back to the fatty alcohol-sugar reaction to make more alkyl polyglycoside. With reuse, the reclaimed fatty alcohol pool has been found to contain increasing amounts of various types of impurities, some of which are generated in the alkyl polyglycoside reaction such as fatty alcohol esters and ethers.

The fatty alcohols typically used in the process according to the invention are those having from 8 to 22 carbon atoms. These alcohols, after having been used in the production of alkyl polyglycoside, are contaminated not only with impurities formed during the alkyl polyglycoside-forming reaction, as set forth above, but can also contain increasing amounts of co-distilling "inert" impurities originally present in the feed alcohol, e.g. hydrocarbons having chain lengths 3 and/or 4 carbons longer than those of the fatty alcohol, and various (e.g. dialkyl and alkyl methyl) ethers of molecular weights similar to the hydrocarbons in question (reference to boiling point relationships in L. F. Fieser and M. Fieser, "Organic Chemistry" p 137, D. C. HEATH and COMPANY, BOSTON (1944)). These "inert" impurities typically arise as by-products in manufacturing processes for naturally-derived fatty alcohols which comprise reacting methyl esters of fatty acids with hydrogen and a catalyst under elevated temperature and pressure conditions. These inert contaminants are not removed by the prior art process which comprise distilling the fatty alcohols in the presence of a base, or simply washing the unreacted fatty alcohols with an aqueous base. This is because these classes of "inerts" cannot react with bases, unlike esters which can partially hydrolyze in the presence of base. Economical separation based on distillation is difficult if not impossible, since the fatty alcohol mixtures in question, and such other impurities as the by-product hydrocarbons derived from higher homologues, ethers and residual fatty alcohol esters of low molecular weight acids, all have very similar boiling points. For example, the boiling point of 1-octanol at 760 mm Hg is 195° C. while at the same pressure the derived octyl formate ester boils at 198° C., and the boiling point at 760 mm Hg for 1-decanol is about 231 ° C. while the boiling point for n-tridecane at the same pressure (atmospheric) is 234° C. As another example, 1-dodecanol and n-pentadecane both boil at 135° C. at 10 mm Hg. These boiling points are close enough at all pressures utilized to obviate inexpensive rectification.

The process according to the present invention provides a means for such rectification via the intermediate formation of polybasic acid esters formed by the reaction of a source of polybasic acid with the recycled fatty alcohols. For purposes of the present invention, a polybasic acid is an acid having more than one acid functionality. Typically, the polybasic acid will be an inorganic acid such as boric acid, phosphoric acid, phosphorous acid, and sulfuric acid. These acids form fatty acid esters which have very high boiling points even at very low pressures. However, a source of an organic polybasic acid could also be used such adipic acid, azelaic acid, or a C-36 dimer acid as long as such an acid is water soluble so that it can be separated by phase separation after the hydrolysis step. The source of the polybasic acid may be the acid itself or a reactive derivative of the acid such as the acid chloride, anhydride, or ester. In the case of inorganic polybasic acids, examples of polybasic acids and/or reactive derivatives thereof include but are not limited to such compounds as boric acid, trimethyl borate, phosphoric acid, phosphoryl chloride, phosgene, phosphorus trichloride, and sulfuryl chloride. The polybasic acid itself should be water soluble so that it can be separated as an aqueous phase after the hydrolysis step. The polybasic acids which can be used in the process according to the invention will be chosen so that the esters they form with the recycled fatty alcohol boil at very high temperatures compared to the non-hydroxylic contaminants in the fatty alcohol. For example, when the polybasic acid is boric acid, the borate esters formed by the claimed process have extremely high boiling points of from about 280°–350° C. (or higher) at 2–3 mm Hg (H. Steinberg, "Organoboron Chemistry", Vol. 1, pp 161–181, John Wiley & Sons, Inc. 1964). Thus, when 3 moles of recycled fatty alcohol are reacted with one mole of a source of boric acid, there is formed a mixture comprising relatively non-volatile, mixed alcohol-borate esters, and various, relatively volatile, non-hydroxylic impurities.

The hydroxylic impurities which can occur in the recycled fatty alcohol are those compounds which have hydroxyl groups or alcohol functionalities capable of reaction with the polybasic acid or source of a polybasic acid. The non-hydroxylic impurities are all the other impurities which do not contain hydroxyl groups or alcohol functionalities. Examples of such non-hydroxylic impurities include, but are not limited to, hydrocarbons, fatty alcohol esters and ethers. Since the boiling point differences between all of the inert impurities or compounds and the polybasic acid esters are so dissimilar, and not unlike the boiling point differences between excess fatty alcohol and alkyl monoglycosides (the most volatile components in the alkyl polyglycosides), these contaminants may be analogously separated based on their volatility. The polybasic acid esters remain in the residual liquid phase. The purified polybasic acid esters are then treated with water (or optionally base) and hydrolyzed to a two phase mixture comprised of a lower aqueous containing polybasic acid (or optionally its salts), and an upper fatty alcohol-containing organic phase, which is substantially free of both non-hydroxylic and color-causing contaminants. The purified fatty alcohol is then dried and recycled into the primary alkyl polyglycoside-forming reaction.

The excess fatty alcohols used in the present invention may be represented by the general formula (I):

$$RO(AO)_nH \qquad (I)$$

wherein R represents a straight-chain or branched alkyl, alkenyl or alkylphenyl group having from 6 to 22 carbon atoms; A represents an alkylene group having from 2 to 4 carbon atoms; and n is a number equal to 0–5.

The above-described excess fatty alcohol is obtained upon separation from a reaction mixture formed in the production of alkyl polyglycosides, an example of which is set out above. The separation may be accomplished by a common distillation procedure comprising heating the reaction mixture under reduced pressure or distillation in a thin film evaporator under reduced pressure. Regardless of the distillation apparatus used, the distillation should occur at a temperature at least 20° C. below the thermal decomposition point of the alkyl polyglycoside components and under reduced pressure.

The excess alcohol, once distilled from the mixture, is then esterified with a source of a polybasic acid. In a preferred embodiment of the invention, using recycled mid-cut alcohol (ave. Mol. wt.=195), from about 8.5 to about 10.5 weight percent of boric acid based on the purity and weight of the fatty alcohol, is reacted with the mixture. The esterification is carried out at a reduced pressure (1–100 mm Hg) and at a temperature in the range from about 50° to about 150° C., preferably from about 80° to about 120° C. for a period of about 1 to about 8 hours. Although the temperature and pressure conditions for water removal are similar to the Fischer Glycosidation reaction, the borate esterification reaction requires no catalyst and no base is required to quench the reaction. Once the esterification reaction is complete, the product formed will be a mixture of borate esters and non-hydroxylic compounds.

As was mentioned previously, due to the significant disparity between the boiling points of the esters of the polybasic acids versus those of the non-hydroxylic compounds, these non-hydroxylic compounds can be easily separated, via the vapor phase, from the polybasic acid esters by means of distillation. The distillation may be carried out at a temperature of from about 160° to about 250° C. and a pressure of about 0.1 to 30 mm Hg using any appropriate distillation apparatus such as, for example, a thin film evaporator.

Once essentially all of the non-hydroxylic compounds have been distilled away, what remains are the esters of the polybasic acids. The next step of the process involves hydrolyzing these polybasic acid esters in order to liberate fatty alcohols and polybasic acid. The hydrolysis reaction can be carried out with water alone or in combination with aqueous base. It is particular advantageous to use water without base when the polybasic acid is boric acid and the boric acid is recycled because boric acid readily crystallizes from water upon cooling (solubility of $B(OH)_3$ per 100 mL $H_2O$=39.1 g@100° C. and 1.95 g@0° C.). The disadvantage of using water is that the hydrolysis of alkyl borates (under neutral or acidic conditions) is, like esterification, an equilibrium reaction, and it is observed that only about 90% of the theoretical amount of boric acid is formed with a single water treatment. In view of the above, it is particularly preferred to employ an aqueous base solution to accomplish the ester hydrolysis. When at least one mole of base is used per mole of boron present, the hydrolysis reaction is driven to completion by conversion of boric acid to its salt. An example of a suitable aqueous base solution is sodium hydroxide added as 50% caustic. Other suitable aqueous base solutions include, but are not limited to potassium hydroxide, calcium hydroxide, sodium carbonate, potassium carbonate, calcium carbonate, sodium borohydride, ammonia and various alkyl amines. As an example, the amount of sodium hydroxide (anhydrous basis) to be added ranges from about 4% to about 10% by weight, depending upon the composition and weight of the borate ester to be hydrolyzed.

The hydrolysis is preferably carried out at a temperature in the range from about 40° to about 110° C. over a period of about 2 hours. Preferably, the reaction is also carried out under agitation so as to ensure a more thorough hydrolyzing reaction.

Once the borate esters have been hydrolyzed, an upper organic phase and a lower aqueous layer are formed. These layers are then separated by drawing off the lower aqueous phase. In a particular embodiment using sodium hydroxide to complete the hydrolysis, the organic layer is then washed with additional water, under agitation, while maintaining the temperature at about 100° C. for a period of about 2 hours. Once again, an organic and water layers are formed, wherein the aqueous layer is again drawn off. The purified fatty alcohols are then recovered from the remaining layer either by drying (e.g. 100° C.@30 mm Hg) or by vacuum distillation at about 0.1 to 10 mm Hg while maintaining the temperature at about 120°–240° C. The substantially pure fatty alcohol is then once again ready for use in the production of alkyl glycosides.

The following examples are illustrative of the present invention and will be useful to one of ordinary skill in the art in practicing the invention. However, the invention should be in no way limited by these examples. Also, unless otherwise indicated, all percentages are by weight.

EXAMPLE

A 20,000 gallon reactor, equipped with an agitator, vacuum system, condenser and receiver was charged with 100,000 pounds of a mid-cut fatty alcohol ($C_{12}$–$C_{16}$, $MW_{ave}$=195), recovered after production of alkyl glycosides, and containing about 12% non-hydroxylic impurities. Anhydrous boric acid (9,500 pounds) was added, and the mixture was agitated and heated to 100° C. under vacuum (20 mm Hg) over a period of 5 hours to remove water (approx. distillate wt.=8,500 pounds). The borate ester-containing mixture (101,000 pounds) was then transferred to a tank and fed at a rate of about 12,000 pounds per hour to a thin film evaporator operating at 220° C. and 2.5 mm Hg. About 13,000 pounds of distillate and 88,000 pounds of residue were collected. The residue together with 55,000 pounds of water were transferred back to the 20,000 gallon reactor. After heating, with agitation to 98° C., the agitator was turned off and two layers allowed to separate. The lower aqueous phase, containing approximately 90% of the starting amount of boric acid, was drawn off and set aside for boric acid recovery. The upper organic phase was treated with 20,000 pounds of water containing 650 pounds of sodium hydroxide for 2 hours at 98° C. The lower aqueous phase, pH=11.8 and containing sodium metaborate, was drawn off and the organic phase washed with an additional 10,000 pounds of water. The lower aqueous phase was again drawn off, and vacuum was carefully applied to finally reach 20 mm Hg. The residue weighed about 86,000 pounds and was 99+% pure alcohol and was used to make more alkyl polyglycoside. The data in Table I below show the composition of untreated, treated, and virgin alcohol. As referred to in the following tables, untreated alcohol is accumulated, recycled alcohol which has not undergone the purification treatment according to the invention. Treated fatty alcohol is alcohol which has undergone the purification treatment according to the invention and virgin alcohol is alcohol as received from a fatty alcohol supplier.

TABLE I

| Identification | Untreated | Treated | Virgin |
|---|---|---|---|
| Total Alcohols | 88.17 | 99.29 | 99.42 |
| Total Hydrocarbons | 2.93 | 0.24 | 0.20 |
| Total Fatty Alcohol Esters | 7.36 | 0.13 | 0.00 |
| Other By-products | 1.06 | 0.31 | 0.38* |
| Total By-products | 11.83 | 0.71 | 0.58 |
| Total Found | 100 | 100 | 100 |

*This number includes $C_{12}$–$C_{16}$ aldehydes and the methyl esters of $C_{12}$–$C_{16}$ fatty acids.

COMPARATIVE EXAMPLE

When treated and untreated recycled alcohols were used to prepare alkyl polyglycoside with an average degree of polymerization of 1.51–1.52, the treated alcohol yielded an alkyl polyglycoside product which was obtained in 13% higher yield, contained 20% less polysaccharide by-products and had a 7-fold decrease in color, relative to the product isolated using untreated alcohol. The properties of the alkyl polyglycosides prepared from the treated and untreated fatty alcohols are listed in Table II below.

TABLE II

| Identification | Untreated | Treated | % Change |
|---|---|---|---|
| % Yield | 31.6 | 35.7 | +13.0 |
| % Polysaccharides | 3.3 | 2.6 | −21.2 |
| Color (Ext. Coefficient) | 8.0 | 1.1 | −86.2 |

What is claimed is:

1. A process for making an alkyl polyglycoside comprising the steps of:

(1) reacting a fatty alcohol having from about 8 to about 22 carbon atoms with a sugar, in the presence of an acid catalyst, to form a product of alkyl polyglycoside and unreacted alcohol, wherein the molar ratio of fatty alcohol to sugar is at least 2:1; (2) separating the excess fatty alcohol from the alkyl polyglycoside product; (3) reacting the separated, excess fatty alcohol with a polybasic acid source to form a mixture comprised of one or more polybasic acid esters and non-hydroxylic compounds; (4) separating the non-hydroxylic compounds by distillation from the polybasic acid esters; (5) forming a substantially pure fatty alcohol by hydrolyzing the polybasic acid esters; (6) returning the substantially pure fatty alcohol to step (1).

2. The process of claim 1 wherein in step (3) from about 6 to about 16 weight percent of a polybasic acid source, based on the amount and the average molecular weight of said excess fatty alcohol, is reacted with said excess fatty alcohol to form at least one ester of said polybasic acid.

3. The process of claim 1 wherein in step (3) said reaction of a polybasic acid source and excess fatty alcohol is conducted at a temperature in the range from about 50° to about 150° C.

4. The process of claim 1 wherein in step (3) said polybasic acid source is reacted with said excess fatty alcohol at a pressure of from about 1 to 100 mm Hg.

5. The process of claim 1 wherein in step (3) said polybasic acid source is reacted with said excess fatty alcohol over a period of from about 1 to about 8 hours.

6. The process of claim 1 wherein in step (4) said non-hydroxylic compound is separated from said polybasic acid esters at a temperature in the range of from about 160° to about 250° C. and a pressure of about 0. 1 to about 30 mm Hg.

7. The process of claim 1 wherein in step (5) said polybasic acid esters are hydrolyzed in the presence of excess water to form an aqueous polybasic acid-containing phase and an organic fatty alcohol-containing phase.

8. The process of claim 7 further comprising the step of removing polybasic acid from said polybasic acid-containing phase and returning said polybasic acid to step (3).

9. The process of claim 7 wherein said polybasic acid ester is hydrolyzed at a temperature from about 40° to about 110° C., over a period of about 2 hours.

10. The process of claim 1 wherein said polybasic acid source is selected from the group consisting of phosphoric acid, phosphoryl chloride, phosgene, phosphorus trichloride, and sulfuryl chloride.

11. The process of claim 1 wherein said fatty alcohol is a compound of the formula (I):

$$RO(AO)_nH \quad (I)$$

wherein R is a straight chain or branched chain alkyl, alkenyl or alkylphenyl group having from 6 to 22 carbon atoms; A is an alkylene group having from 2 to 4 carbon atoms; and n is a number 0 to 5.

12. The process of claim 1 wherein following step (5) and prior to step (6) the substantially pure fatty alcohol is either dried or vacuum distilled to remove water therefrom.

13. The process of claim 1 wherein step (2) is carried out by distillation under reduced pressure at a temperature at least 20° C. below the thermal decomposition temperature of the alkyl polyglycoside; step (3) is carried out at a temperature in the range of from about 50° to about 150° C.; step (4) is carried out at a temperature in the range of from about 160° to about 250° C. and at a pressure of from about 0.1 to about 30 mm Hg; and step (5) is carried out with excess water or an aqueous base as the hydrolyzing agent.

14. A process of making an alkyl polyglycoside comprising the steps of: (1) reacting a fatty alcohol having from about 8 to about 22 carbon atoms with a sugar, in the presence of an acid catalyst, to form a product of alkyl polyglycoside and unreacted alcohol, wherein the molar ratio of fatty alcohol to sugar, respectively, is at least 2:1; (2) separating the excess fatty alcohol from the alkyl polyglycoside product; (3) reacting the separated, excess fatty alcohol with a source of boric acid to form a mixture comprised of one or more borate esters of the fatty alcohol and non-hydroxylic compounds; (4) separating the non-hydroxylic compounds by distillation from the borate esters; (5) forming a substantially pure fatty alcohol by hydrolyzing the borate esters; (6) returning the substantially pure fatty alcohol to step (1).

15. The process of claim 14 wherein in step (5) said borate esters are hydrolyzed in the presence of an aqueous base, wherein the mole ratio of base to borate esters is from about 1.0 to about 1.5, to form an aqueous borate salt-containing phase and an organic fatty alcohol-containing phase.

16. The process of claim 15 wherein said borate esters are hydrolyzed at a temperature from about 40° C. to about 110° C., over a period of about 2 hours.

17. The process of claim 15 further comprising the step of washing said hydrolyzed borate esters with water.

18. The process of claim 14 wherein said source of boric acid is trimethylboron.

19. The process of claim 14 wherein said source of boric acid is boric acid.

20. The process of claim 14 wherein in step (3) from about 6 to about 16 weight percent of boric acid, based on the amount and average molecular weight of said excess fatty alcohol, is reacted with said excess fatty alcohol to form said borate esters.

21. The process of claim 14 wherein in step (3) said reaction of boric acid and excess fatty alcohol is conducted at a temperature in the range from about 50° to about 150° C.

22. The process of claim 14 wherein in step (3) said boric acid is reacted with said excess fatty alcohol at a pressure of from 1 to 100 mm Hg.

23. The process of claim 14 wherein in step (3), said boric acid is reacted with said excess fatty alcohol over a period of from about 1 to about 8 hours.

24. The process of claim 14 wherein in step (4) said non-hydroxylic compounds are distilled from said borate esters at a temperature in the range of from about 160° C. to about 250° C. and a pressure of about 0.1 to about 10 mm Hg.

25. The process of claim 1 wherein in step (5) said borate esters are hydrolyzed in the presence of excess water or aqueous base to form an aqueous boric acid-containing phase and an organic fatty alcohol-containing phase.

26. The process of claim 14 where said fatty alcohol is a compound of the formula (I):

$$RO(AO)_nH \quad (I)$$

wherein R is a straight chain or branched chain alkyl, alkenyl or alkylphenyl group having from 6 to 22 carbon atoms; A is an alkylene group having from 2 to 4 carbon atoms; and n is a number 0 to 5.

27. The process of claim 14 wherein following step (5) and prior to step (6) the substantially pure fatty alcohol is either dried or vacuum distilled to remove water therefrom.

* * * * *